United States Patent [19]
Williams et al.

[11] Patent Number: 6,146,838
[45] Date of Patent: *Nov. 14, 2000

[54] DETECTING WATER-BORNE PARASITES USING ELECTROCHEMILUMINESCENCE

[75] Inventors: Richard O. Williams, Potomac; John H. Kenten, Boyds, both of Md.

[73] Assignee: IGEN International, Inc., Gaithersburg, Md.

[ * ] Notice: This patent issued on a continued prosecution application filed under 37 CFR 1.53(d), and is subject to the twenty year patent term provisions of 35 U.S.C. 154(a)(2).

[21] Appl. No.: 08/820,017

[22] Filed: Mar. 18, 1997

[51] Int. Cl.$^7$ ........................ G01N 33/53; G01N 33/531; G01N 33/553; G01N 33/541
[52] U.S. Cl. ........................ 435/7.2; 435/7.22; 435/7.92; 435/961; 435/968; 435/973; 435/975; 435/971; 436/526; 436/540; 436/177
[58] Field of Search ..................................... 435/7.2, 7.22, 435/7.92, 961, 968, 973, 975, 971; 436/526, 540, 177

[56] References Cited

U.S. PATENT DOCUMENTS

| | | | |
|---|---|---|---|
| 5,466,416 | 11/1995 | Ghaed et al. | 422/52 |
| 5,556,774 | 9/1996 | Wiedenmann et al. | 435/91.2 |
| 5,677,192 | 10/1997 | Klemt et al. | 436/172 |
| 5,690,825 | 11/1997 | Parton | 210/350 |

FOREIGN PATENT DOCUMENTS

| | | |
|---|---|---|
| WO89/04302 | 5/1989 | WIPO . |
| WO90/05296 | 5/1990 | WIPO . |
| WO90/05302 | 5/1990 | WIPO . |
| WO92/14138 | 8/1992 | WIPO . |

OTHER PUBLICATIONS

Robertson et al., "In Vitro Excystation of *Cryptosporidium parvum*," Parasitology, 106 (Part 1):13–19, Jan. 1993.

Campbell et al., "Detection of Oocysts of Cryptosporidium by Enhanced Chemiluminescence," J. of Microbiol Methods, 17: 297–303, 1993.

Johnson et al., "Quantitative Assay Development for Cryptosporidium" FASEB Journal, 9 (3 Part I): A229, Abstract No. 1328, Mar. 9, 1995.

Johnson et al., "Development of a PCR Protocol for Sensitive Detection of Cryptosporidium Oocysts in Water Samples," Applied Environ. Microbiol. 61(11): 3849–3855, Nov. 1995.

Jakubowski et al., "Environmental Methods for Cryptosporidium," American Water Works Association Journal. 88(9):107–121, 1996.

Primary Examiner—Nita Minnifield
Assistant Examiner—Padma Baskar
Attorney, Agent, or Firm—Whitman Breed Abbott & Morgan

[57] ABSTRACT

A method for the detection or quantitation of a water-borne parasite, such as Cryptosporidia. The detection or quantitation is accomplished by an electrochemiluminescence assay comprising the steps of filtering water to obtain a sludge thought to contain the parasite or a fragment thereof; extracting a sample of said sludge in a extraction medium to form antigenic derivatives of said parasite; forming an assay mixture comprising a sample of said extracted sludge and an antibody specific to said antigenic derivative; incubating said assay mixture to permit binding of said antibody and said antigenic derivative; and conducting an electrochemiluminescence assay for the bound complex of antibody and antigenic derivative, thereby detecting or quantitating the Cryptosporidia in said water.

31 Claims, No Drawings

DETECTING WATER-BORNE PARASITES USING ELECTROCHEMILUMINESCENCE

BACKGROUND

Cryptosporidium and CryDtosporidiosis

Cryptosporidium is a genus of protozoan parasite commonly found in the gastrointestinal tract of vertebrates. There are eight named species of Cryptosporidium, C. parvum is infectious for 79 species of mammals, including humans, causing acute gastroenteritis. Unlike most parasites, C. parvum lacks host specificity among mammals and is able to cross- infect multiple host species.

Cryptosporidiosium is transmitted as an oocyst via the fecal-oral route. Contaminated water, close human-to-human contact and contact with the excrement of infected livestock, zoo animals or domestic animals can lead to transmission of the parasite. When outside a host, the exogenous phase, Cryptosporidium exists as a sporulated oocyst. The oocyst consists of four sporozoites within a tough, two layered wall. The oocyst wall has defined inner and outer layers and a suture at one end. During excystation, the suture dissolves providing an opening through which the sporozoites leave the oocyst. When ingested by a suitable host, excysted sporozoites, the living matter, parasitize the cells of the gastrointestinal or respiratory tract. After reproduction, resporulation into oocysts occurs. Oocysts in the gastrointestinal tract are excreted with the fecal matter while those in the respiratory tract exit the body in respiratory and nasal secretions.

Cases of infection by Cryptosporidium are commonly encountered in both developed and underdeveloped countries. The slightly higher prevalence of Cryptosporidiosis in the lesser developed countries can be attributed to poor sanitation, malnutrition, contaminated drinking water and close contact with infected persons and animals.

The most common clinical sign associated with Cryptosporidiosis is diarrhea, which can be severe and result in weight loss and dehydration. Other common clinical symptoms include abdominal cramps, fever, nausea, vomiting, headache, fatigue, myalgia and inappetence. Infections with Cryptosporidium are generally in the small intestine, but have also occurred in the lungs, esophagus, stomach, and other organs. The clinical symptoms associated with the parasitic infection depend on the affected organ.

The range of symptoms and the severity of the illness can vary greatly from one individual to another and can become life threatening. The symptoms of acute enteritis generally last one to two weeks in individuals who are otherwise immunologically healthy. Cryptosporidiosis represents a heightened threat in AIDS patients, malnourished persons, individuals with inherited immune deficiencies, and person receiving immunosuppressive drugs.

All infections with Cryptosporidium are initiated by ingestion or inhalation of the oocyst. Because the parasite is transmitted in the form of an oocyst, oocysts have evolved to survive in harsh environmental conditions and are unusually resistant to natural stresses and chemical disinfectants. In addition, the presence of an exogenous oocyst encapsulating the protozoan parasite makes the parasite much more resistant to conventional water treatment processes. Measures to prevent or limit the spread of infection concentrate on eliminating or reducing infectious oocysts in the environment. For humans, disinfection procedures are sought to minimize person-to-person transmission and to deal effectively with contamination of water supplies.

The fairly recent occurrence of large water-borne outbreaks has focused attention on the importance of understanding their transmission through the environment. Surface waters may be polluted naturally by infected animal excrement. Many waste disposal practices may lead to contaminated water courses and streams. Fecal contamination of waterways has recently led to massive outbreaks of C. parvum infection. Water polluted by these practices may then lead to the contamination of drinking water supplies or of food crops during irrigation.

Chemical Composition and Decomposition of Cryptosporidium

The protein, carbohydrate, and lipid composition of C. parvum is diverse and complex. Many of the components are antigenic and therefore function as immune response targets. Glycoproteins ranging from <14 to 7200 kDA from disrupted oocytes, purified oocyst shells and purified sporozoites have been identified by SDS-PAGE gel electrophoresis. Many of these oocyte-derived proteins are glycosylated. Specific carbohydrate moieties have been identified. It has been determined that sporozoite glycoproteins with terminal N-acetyl-D-glycosamine residues may function in attachment of the parasite or somehow assist in invasion. These carbohydrates are expressed on the oocyte surface and are useful in immunological detection methods. sporozoites of Cryptosporidium can spontaneously excyst through a suture at one pole of the oocyst when warmed to about 37° for approximately 90 minutes. This renders mechanical methods for oocyst wall disruption unnecessary to accomplish.

Pretreatment of C. parvum oocytes with sodium hypochlorite (a "bleach") results in separation of the inner and outer oocyst walls. That is, while it is not necessary to pretreat oocysts within a reducing agent when excysting C. parvum, a slight increase in the rapidity of excystation occurs when bleach treated oocysts are incubated in PBS containing 0.01M cysteine HCL during the excystation process. Oocysts that have not been pretreated with bleach excyst somewhat when they are warmed to approximately 37° C. The use of trypsin and bile salts, or bile salts alone, can increase or speed excystation of unbleached oocysts.

Prior Art Assay Methods for Crytospyridium

Immunological techniques have been used to detect C. parvum in environmental specimens. The availability of monoclonal antibodies for specific antigens of Cryptosporidium facilitated development of these methods.

Immunofluorescence assays (IFA) are the most common assays used to detect Cryptosporidium oocytes in specimens and to detect the presence of a specific antibody. These methods employ fluorescent dyes which are combined with antibodies to make them fluoresce when exposed to ultraviolet light. In a typical IFA assay, water is filtered through a polypropylene cartridge filter or a flat, membrane filter. Both filters yield filtrates that are then subjected to purification before analysis by microscopy. The filtrate is removed from the filter and then centrifuged. Extraneous debris is removed by flotation over a sucrose solution. The supernatant is labeled with a fluorescein conjugated antibody against Cryptosporidium and examined by epifluorescence microscopy.

Some commercial immunofluorescent assays and reagents used to detect Cryptosporidial oocytes include: (1) HydroFluor Combo, an immunofluorescent assay system based on an oocyst-specific monoclonal antibody (IgM, OW3) (2) Detect IF Cryptosporidium, an immunofluorescent assay system based on an oocyte-specific monoclonal antibody (IgM, C1), and (3) Crypto IF Kit, an immunofluorescent assay system based on an oocyst-specific monoclonal antibody.

The disadvantages of immunofluorescence assays include their low recovery efficiency, long processing times, the need for highly trained analysts, high cost, the inability to discriminate viable or virulent strains and cross-reactivity of the probes with similar size and shaped algae. In addition, IFA detection often involves the time consuming and skill intensive step of looking at water sludge under a microscope for oocysts that have been labeled with a fluorescent antibody. It is also often difficult to distinguish oocysts from debris bound non-specifically by the antibodies. The procedure is expensive and often takes days to complete.

Enzyme-linked immunosorbent assays (ELISA) using oocyte-reactive monoclonal antibodies is also used to detect Cryptosporidium in contaminated water samples. Two basic ELISA tests have been used in the past for detecting Cryptosporidium antigen in samples: (1) the double antibody sandwich technique for the detection of antigens, and (2) the enzyme-linked indirect immunosorbent assay for the detection of antibodies.

In the double antibody sandwich method, antiserum is adsorbed to a well. Test antigen is added and, if complementary, binds to the antibody. An enzyme-linked antibody specific for the test antigen then binds to the antigen, forming a sandwich. The enzyme's substrate is then added, and the reaction produces a visible color change. In the indirect immunosorbent assay, an antigen is adsorbed to a well. Test antiserum is then added, with complementary antibody binding to the antigen. Enzyme-linked anti-human gamma globulin is then added. It binds to the bound antibody. The enzyme's substrate is then added, producing a visible color change. A difficulty encountered in enzyme-based assays is the deactivation of the enzyme by components of the assay mixture. A further difficulty is encountered in the wash step where strong forces overcome the antibody-antigen interaction. This leads to loss of assay precision.

Detection assays based upon polymerase chain reactions (PCR) have also been used to detect oocysts in clinical or environmental samples. Several DNA and RNA regions of C. parvum have been sequenced and have been reported to be assay targets for parasite detection.

Flow cytometry is another method used to detect parasitic contamination of water samples. Flow cytometry techniques can quantify whole oocysts but involves much preparation, and time and require extremely expensive equipment.

Numerous problems are associated with prior art methods of detecting Cryptosporidium in water and environmental samples. In addition to those mentioned and the general lack of precise, recitable assays, prior art techniques generally require that samples be transferred to a laboratory or to another remote location for the conduct of the assay. Prior art techniques lack the requisite reliability, speed and sensitivity to accurately detect Cryptosporidium in contaminated water samples.

The detection of infectious C. parvum oocysts in water and other environmental samples is essential to detecting and treating contaminated water supplies. It is crucial, therefore, that specific, rapid and highly sensitive assays be developed to detect the presence of the parasite accurately and reliably. The known methods of enzyme immunoassays and immunofluorescence do not fulfill these requirements. The source, viability and pathogenicity of oocysts found in water or other environmental samples cannot be reliably determined using prior art methods. There is a need for routine epidemiological surveillance and environmental monitoring that can be conducted on site to provide early detection of the parasite.

OBJECTS OF THE INVENTION

A primary object of this invention is to provide a fast, sensitive, and precise assay for the detection or quantitation of oocysts of Cryptosporidium in environmental samples.

It is another object of this invention to provide a fast, sensitive, and precise assay procedure for the detection or quantitation of sporozoites of Cryptosporidium in an environmental sample.

It is a further object of this invention to provide a fast, sensitive, and precise assay procedure for the contemporaneous detection and quantitation of oocysts and sporozoites of Cryptosporidium in an environmental sample.

Still a further object of the invention is to provide rapid quantitative assays for C. parva in decentralized settings, i.e., at water treatment plants, which are not labor-intensive and which employ reliable assay instruments.

SUMMARY OF THE INVENTION

The problems inherent in the prior art assays are solved in the electrochemiluminescence (ECL) based assays of the invention. These assays can detect Cryptosporidium in water sources. These ECL assays are rapid assays for the detection or quantitation of *C. parva* in decentralized settings, i.e., the water is assayed at the treatment plant. The simple quantitative assays are a major improvement over the prior art methods. They are precise and sensitive and are performed in a few hours without extensive labor.

The assays can detect or quantify whole oocysts or fragments of oocysts using a method that is reliable, accurate and inexpensive, and can be performed rapidly using simple equipment.

This invention is broadly in a method for the detection or quantitation of Cryptosporidium in water by an electrochemiluminescence assay comprising the steps of:

a) filtering water to obtain a sludge containing oocysts of Cryptosporidia;

b) extracting a sample of the sludge in an extraction medium to form at least one antigenic derivative of the oocysts;

c) forming an assay mixture comprising a sample of the extracted sludge and an antibody specific to the antigenic derivative;

d) incubating the assay mixture to permit binding of the antibody and the antigenic derivative; and e) conducting an electrochemiluminescence assay for the bound complex of antibody and antigenic derivative and thereby detecting or quantitating Cryptosporidia in the filtered water.

The assay mixture contains a sample of extracted sludge, magnetic particles labeled with a first antibody specific to a first epitope of the antigenic fragment, a labeled probe comprising a second antibody specific to a second epitope of the antigenic derivative, and an ECL assay reagent. The second epitope may be the same as or different from the first epitope.

The method of the invention can also be used for the detection or quantitation of sporozoite antigens of Cryptosporidia and to assays in which the Cryptosporidia oocysts' outer wall and sporozoites contained in the oocysts are assayed contemporaneously.

The invention also relates to a kit for conducting the electrochemiluminescence assays for Cryptosporidia in water which includes an extraction medium for the extraction of antigenic derivations in oocyst walls and/or sporozoites from organic sludge obtained from water filtration and an antibody specific to an antigenic derivative in the extracted sludge. Kits for the conduct of an electrochemiluminescence assay for Cryptosporidium in water may also include components of an electrochemiluminescence assay, including magnetic particles labeled with an antibody specific to an epitope of an antigenic derivative of extracted Cryptosporidia oocysts, ECL label probes comprising an antibody specific to an epitope of the antigenic derivative, and assay reagents.

The methods and assays for detecting Cryptosporidium in environmental samples offer distinct advantages over prior art detection methods. The assay can be conducted on the raw sludge, at the site of filtration, i.e. in a decentralized setting, so that there is no need to transport the specimens to another location for analysis. The results obtained using this invention are precise, accurate, rapid and overcome the problems inherent in prior art procedures.

DETAILED DESCRIPTION OF THE INVENTION

The invention is in an electrochemiluminescence assay for the detection of Cryptosporidia in sludge obtained from a raw water filter. The presence and amount of both oocysts and/or sporozoites can be determined in these assays. Thus, the assay can detect if the water is presently contaminated with living parasites or if only empty oocysts remain in the water sample. Sludge collected from a filtrate of raw water is treated directly to release antigens in soluble form from the parasites for detection.

Living and dead parasites can be detected from the filtrate sample. The assay therefore provides qualitative or quantitative information regarding previous contamination of the water (no viable parasites) as well as regarding present contamination (infective, sporozoite-containing parasites).

The method generally comprises the steps of:
a) filtering the water to obtain a sludge containing oocysts of Cryptosporidia;
b) extracting a sample of the sludge in an extraction medium to form derivatives of oocysts including at least one antigenic derivative;
c) forming an assay mixture comprising a sample of the extracted sludge and an antibody specific to the antigenic derivative;
d) incubating the assay mixture to permit binding of the antibody and the antigenic derivative; and
e) conducting an electrochemiluminescence assay for the bound complex of antibody and antigenic derivative and thereby detecting or quantitating the Cryptosporidia.

Glycosylated proteins in the walls of the oocysts and sporozoite serve as antigenic derivatives for these assays. The protein, carbohydrate, and lipid composition of *C. parvum* is diverse and complex. Many of these are antigenic and thus function as immune-response targets. Identification and characterization of *C. parvum* antigens has been facilitated by protocols for purifying oocysts and sporozoites. Many protein/glycoprotein molecules from disrupted oocysts, purified oocyst shells and purified sporozoites, ranging from <14 to 7200 KDA have been identified in protein-stained sodium dodecyl sulfate-polyacrylamide gel electrophoresis (SDS-PAGE) gels. Monoclonal antibodies specific to these glycosylated proteins in the wall of the oocyst and the sporozoite can be used in these immunoassays.

The mAb OW3 identifies *C. parvum* sporozoite cDNA that encodes a putative 670 amino acid sequence with significant homology to both hsp70 and a 78 kDa glucose regulation protein. This mAb recognizes a >200-kD *C. parvum* oocyst wall antigen on western blots. Although this molecule may be a component of the oocyst wall, the Gly-Gly-Met-Pro repeat of *C. parvum* hsp70 should be highly immunogenic and may simply have an antigenic feature in common with COWP-190. The mAb OW-IGO, developed to detect antigenic moieties within the outer wall of *C. parvum* oocysts, also labels the fibrillar material in the parasitophorous vacuole of developing macrogametes, microgametocytes, and sporulating oocysts. On western blots, the antibody recognizes major bands at 250 and 40 kDa and additional smaller bands. Most western blot activity is abolished by periodate treatment, again suggesting carbohydrate on the outer wall.

The sludge collected from a filtrate of raw water is treated to release the antigens from the parasites so that they can be detected by immunoassays. The extraction and solubilization of the antigens requires an acid treatment of the parasites in the presence of bile salts at approximately 40° C. This treatment activates protease enzymes that help to break down the oocysts walls. The sample is then treated with a base such as tris to provide a pH between 5.5 and 8. The sample is then treated with disruptive agents such as ionic or non-ionic detergents and/or urea or formamide incubated at elevated temperatures in buffered solutions. The sample may then be treated with reducing agents such as mercaptoethanol or dithiolthreitol. Excess bile salts or detergent-reagents can be removed or sequestered by adding different non-ionic detergents or BSA or other animal serum albumin or immunoglobulin to the extract, leaving the target antigens in solution and in a state ready to bind with specific complementary antibodies. Excess chaotropic agents can be removed by dialysis or enzymatic means or chromatography, or their effects by dilution. Excess reducing agents may be removed by treatment with: oxygen (or air) saturated buffer, diamide, iodine solution (0.05 N in water), tert-butyl hydroperoxide, ferricyanide, hydrogen peroxide, iodoacetomide, N-methyl maleimide, 2-(2-pyridyl dithio) ethanol.

The assays of the invention employ procedures for treating the parasite oocytes with bile salts at elevated temperatures, in vitro, to induce excystation and to release antigens from both the oocysts and the sporozoites. These antigens can then be detected and quantitated in an immunoassay.

The antigens in solution in the treated sludge suspension, consisting of antigens released from the oocyst membranes and the sporozoites, if any, are incubated with antibodies specific for the antigenic derivatives, e.g., antibody OW3 which is specific for an oocyst wall antigen of >20okD. Antibody OW3 recognizes linear repetitive epitopes characterized from Western blot experiments. Linear epitopes are not destroyed after detergent treatment and therefore remain active with antibodies following solubilization of the sludge. Once the antigens are in solution, the ECL immunoassay can be conducted.

ECL assay techniques provide a sensitive and precise measurement of the presence and concentration of an analyte of interest. In such techniques, electrochemiluminescence is triggered by a voltage impressed on the working electrode of an ECL cell at a particular time and in a particular manner. The luminescence produced by the ECL label is measured and indicates the presence or quantity of the analyte.

Electrochemiluminescence assays can be performed with or without the need for a separation step during the assay procedure and at maximum signal modulations for different concentrations of analyte, so that precise and sensitive measurements over a broad range of concentration of analyte can be made. Nonseparation assays include those which employ microparticulate matter suspended in the assay sample to bind one or more of the binding components of the assay.

For a fuller description of ECL techniques, reference is made to PCT published application U.S. Ser. No. 85/01253 (WO86/02734), PCT published application number U.S. Ser. No. 87/00987 (WO 87/06706), and PCT published application U.S. Ser. No. 88/03947 (WO89/04302). These publications and those referred to below are incorporated by reference. While it had been expected in the art that luminescence from electrochemiluminescent moieties would be absorbed, scattered, or otherwise suffer interference from the microparticulate matter, U.S. application Ser. No. 539,389 now abanoned, continued by U.S. application Ser. No. 08/413,336 (PCT published application U.S. Ser. No. 89/04919(WO90/05301)) teaches sensitive, specific binding assay methods based on a luminescent phenomenon wherein inert microparticulate matter is specifically bound to one of the binding reactants of the assay system. The assays of that application may be performed in a heterogeneous (one or more separation steps) assay format and may be used most advantageously in a homogeneous (nonseparation) assay format.

The signal from labeled species can be enhanced by concentrating them before subjecting them to a measurement step. U.S. application Ser. No. 08/255,824 now U.S. Pat. No. 5,705,402 PCT published application U.S. Ser. No. 92/00982 (WO92/14138) relates to a method of particle based electrochemiluminescence measurement wherein particles are brought into close contact with the electrode using a magnet to impose a magnetic field which collects the particles at the electrode.

Particles useful in electrochemiluminescence assays advantageously have a diameter of 0.01 to 200 $\mu$m and a surface component capable of binding, directly or directly, to the analyte. The particles are suspended in the ECL system, and are advantageously magnetically responsive.

The assay requires an electrolyte. Generally, the electrolyte is in the liquid phase, for instance as a solution of a salt in water. The electrolyte is, in certain embodiments of the invention, a buffered system such as an aqueous solution of sodium phosphate/sodium chloride or an aqueous solution of sodium phosphate/sodium fluoride.

As described in PCT published application U.S. Ser. No. 89/04859 (WO90/05296), it is desirable to include a reductant, typically an amine or amine moiety (of a larger molecule) which can be oxidized and spontaneously decomposed to convert it into a highly reducing species, which in turn facilitates the electrochemiluminescent phenomenon. A wide range of amines and corresponding amine moieties can be utilized in practicing the present invention. Amines (and corresponding moieties derived therefrom) which are advantageously utilized in the present invention, including aliphatic amines, such as primary, secondary and tertiary alkyl amines, the alkyl groups of each having from one to three carbon atoms, as well as substituted aliphatic amines. Tripropyl amine is especially preferred.

As described in PCT published application U.S. Ser. No. 89/04915 (WO 90/05302) the assays of the invention are desirably carried out in the presence of an enhancer utilized in an amount sufficient so that in its presence the desired increase in emission of electromagnetic radiation, typically a compound of the formula

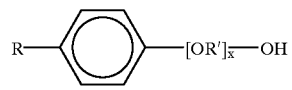

wherein R is hydrogen or $C_nH_{2n+1}$, R' is $C_nH_{2n}$, X is 0 to 70, and n is from 1 to 20.

The apparatus for carrying out the assays of the invention includes a working electrode or other triggering surface to apply an electric potential to trigger the reactions which cause the particle-linked ECL moiety to electrochemiluminesce and magnets capable of collecting the particle-linked ECL moiety at the electrode. Further details of apparatus for carrying out the ECL assays of the invention are disclosed in published PCT applications U.S. Ser. No. 89/04854 (WO 90/05411) and U.S. Ser. No. 90/01370 (WO 90/11511).

The assays of the invention can be performed in any of the conventional formats, i.e., direct, indirect, forward, reverse or competitive formats. Sandwich immunoassays, as are well known in the field of diagnostics in general and in ECL detection specifically, are preferred. Such assays involve an analyte (antigen) which is bound by two antibodies: a "primary" or capture antibody which is bound to a solid surface by, for example, being labeled with biotin, and a "secondary" or label antibody which is labeled with an electrochemiluminescent species such as $Ru(bpy)_3^{2+}$. Hence, in such an assay, a streptavidin-coated solid support is bound to a biotinylated primary antibody. The primary antibody is bound to the analyte (the antigen, if present), which antigen is bound to the $Ru(bpy)_3^{2+}$- labeled secondary antibody.

In the invention, a monoclonal antibody specific to a first epitope of an antigen of interest—OW3 in the case of an assay for oocyst antigens, E3E in the case of an assay for sporozoite antigens—is conjugated to biotin. A monoclonal antibody specific to a second epitope of the antigen of interest (which may be the same as the first epitope) is conjugated to an ECL label ("TAG"). The extracted sludge and a solution of the biotinylated primary antibody are combined and incubated. The TAG-labelled antibody is then added and incubated to permit binding of TAG-labelled antibody and analyte. Following this incubation, a suspension of streptavidin coated beads is added to combine with the biotin on the primary antibody.

The oocyte antigen immune complex is detected using an analyzer such as the ORIGEN® Analyzer. ORIGEN® Analyzers and reagents are available from Igen, Inc., Gaithersburg, Md. The immune complex that is quantitated in this procedure consists of the streptavidin coated paramagnetic beads bound by biotin to the complex of the antibody, OW3, which is bound to the OW3 specific antigen, which in turn is bound to another OW3 antibody, conjugated to the electrochemiluminescent moiety that produces the light in the analyzer. The magnetic beads and bound sandwich are brought to the surface of the electrode by a magnet associated with the flow cell. A voltage is applied to the electrode. Light produced by the ECL moiety is detected and quantitated by a photomultiplier.

The solubilized material generated in the treatment of the sludge collected from the water filter includes all of the antigenic derivatives from *C. parvum* in the filtered water. Thus, a single preparation of solubilized material can be used to assay for both the Cryptosporidium oocyst and the sporozoites that it contains. It is important to quantitate both the number of viable sporozoites in the water, because they constitute the human-infective form of the parasite, as well as the oocysts from which they may have been liberated. The latter measurement may represent a present concentration of viable oocysts or a concentration of inviable oocysts, revealing a history of the contamination.

Monoclonal antibody, 3E3, is specific for the highly immunogenic 27kD sporozoite surface antigen (p27). The 3E3 monoclonal antibody is conjugated to biotin and purified from the reaction mixture. A polyclonal antiserum prepared to the same highly immunogenic 27 kD sporozoite surface antigen (p27) is conjugated to a TAG and is then purified from the reaction mixture. A solution of the biotinylated antibody (in an assay diluent) is added to the treated sludge and incubated for about 1 hour at about 37° C. The solution of the TAG-labelled antiserum (in assay diluent) is then added to the mixture and incubated under the same conditions. Following this incubation, a suspension of streptavidin coated beads are added and incubated for about 30 minutes at room temperature. The sporozoite antigen immune complex is detected using an Analyzer (such as the ORIGEN Analyzer) as described above.

The detection or quantitation assays for one or both of the oocyst or sporozoite antigens can be performed essentially contemporaneously, i.e., one after the other. A significant advantage over the prior art methods is that one can determine if the water sample is actually infected with live sporozoites or whether there are merely non-infectious empty oocytes present. In addition the sludge collected on the water filter can be analyzed directly without extensive pretreatment.

The method and assay of the invention are described further with reference to the following examples.

EXAMPLES

Example 1

WATER SAMPLE COLLECTION 100 to 1000 liters of potable/clean water is filtered through a cuno-type filter. The filter membrane along with the sludge filtrate is cut free and removed from the holder. The membrane sheet is placed in a plastic container and 1 liter of a 0.1% Tween 80™ detergent solution is added to the container. The filter is agitated for 20 minutes and the sludge suspension is decanted into a centrifuge bottle. A second 1 liter of detergent solution is added to the container and the filter is agitated again for 20 minutes. The second liter is then decanted into a centrifuge bottle and the 2 liters of sludge filtrate suspension is centrifuged at 7,280 g for 12 minutes. The bottles are removed from the centrifuge and the supernatant liquid is carefully aspirated off to leave a pellet in approximately 20 to 30 mls liquid in the bottles. The remaining liquid is vigorously shaken to resuspend the pellet and transferred to a 50 ml centrifuge tube. The bottle is rinsed with a 0.1% Tween™ 80 solution and added to a 50 ml centrifuge tube using ≈5 ml distilled water, if necessary, to balance the centrifuge tubes. The 50ml tubes are centrifuged at 2190 g for 10 minutes, and the supernatant liquid is decanted. The 2 pellets are pooled and resuspended. The final volume of the concentrate is measured in microliters with a pipetman.

Example 2

SOLUBILIZATION OF THE CRYPTOSPORIDIUM ANTIGENS

50% of the volume of the resuspended concentrate derived in Example 1 is pippetted into a clean 50 ml centrifuge tube. A 10× concentrated stock solution of Hanks basic salt solution (HBSS) is adjusted to pH 2.5 with HCl. A predetermined amount of the low pH HBSS 10× concentrate and predetermined amount of a 5% stock solution of bovine bile salts are added to the sludge suspension to give final concentrations of 0.5% bile salts and 1× HBSS. The sludge suspension is then incubated at 40° C. for 2 hours. After incubation, the solution is adjusted to pH 7 with tris base and a 3% stock solution of sodium dodecyl sulfate is added to give a final concentration of 0.3%. A predetermined amount of 200 mM mercapto-ethanol or 100 mM dithiothreitol is added to give a final concentration of 20 mM mercapto-ethanol or 10 mM dithiothreitol. The suspension is mixed and incubated at 40° C. for 1 hour. N-methylmaleimide is added to a final concentration of 20 mM. 5% stock solution of Triton X-100™ is added to give a final concentration of 0.5% and bovine serum albumin is then added to the incubation mixture to a final concentration of 2% to sequester excess detergent and thereby improve immunoreactivity in the presence of the detergents. The solution is mixed and the final volume of the extraction mixture is measured in microliters with a pipetman.

This extract is equivalent to 50% of the volume passed through the filter. The volume of the extract to be analyzed can be calculated as follows: Divide the extract volume in microliters by half the number of liters of water sampled. This will yield a volume ratio of microliters extract per liter of water sample. The water sample-equivalent to be analyzed should be at least 10% of the water volume passed over the filter. Thus 20% of the extract should be analyzed. The immunoassay volume to be analyzed should be between 20 and 50 microliters.

Example 3

PREPARATION OF OW3/ORIGEN TAG-NHS ESTER CONJUGATE 0.5 mg of OW3 protein are dissolved in 500 µl of PBS, pH 7.8, in a polypropylene vial. Ultra-filtration concentrating devices are used to achieve buffer exchange and concentration of the protein. ORIGEN TAG-NHS Ester stock solution is prepared by adding 50 µl of DMSO to the 75 µg vial of TAG-NH3 Ester (Igen). The vial is gently twirled to wet the bottom and lower sides of the vial with the DMSO. This volume of DMSO dissolves the 75 µg ORIGEN TAG-NHS Ester, resulting in 1.5 µg/µl stock solution.

A 25:1 molar ratio of ORIGEN TAG-NHS Ester is added to the above OW3 solution at 1 mg/ml. Based on molecular weights of 1057 and 750,000, respectively, 35 µg/ml of the ORIGEN TAG-NHS Ester is added to the protein solution. The remaining ORIGEN TAG-NHS Ester is discarded. Vial contents are vortexed and incubated in darkness at room temperature for 60 minutes. The reaction is stopped by adding 20 µl of 2 M glycine and incubating in darkness at room temperature for an additional 10 minutes.

Uncoupled ORIGEN TAG label is removed by loading the mixture onto a PD-10 column (a prepacked Sephadex™ G-25 column manufactured by Pharmacia) previously equilibrated with PBS containing sodium azide or thimerosol. Due to the column's long separation time, it is covered with aluminum foil to shield the conjugate from the light. Two yellow bands formed as the separation of bound from free ORIGEN TAG proceeded. The labeled protein eluted first, followed by a second band corresponding to unconjugated ORIGEN TAG. Eight 0.5 ml fractions are collected after the sample volume entered the resin bed.

Protein concentration in moles per liter was determined by using a standard protein assay (e.g., Bradford, Lowry, or a Pierce BCA protein Assay kit). An absorbance reading at an OD of 280 nm is avoided since TAG does alter the absorbance at this wavelength. The protein-containing fractions are collected and pooled to determine the final pooled protein concentration and molarity. The percent protein recovered ranged from 70–90%, depending on the separation technique employed.

The absorbance of the TAG-OW3 at 455 nm is measured by using a 1 cm path cuvette. The absorbance value is divided by 13,700 to obtain the ORIGEN TAG concentration in moles per liter.

The ORIGEN TAG:OW3 ratio is calculated by dividing the previously obtained value for ORIGEN TAG concentration by the previously obtained value for protein concentration.

LABELLING OF THE P27 ANTIGEN RECOGNIZING ANTIBODY

Sporozoite (p27) antigen was prepared by immunopurification on a solid phase using 3E3 antibody from extracts prepared as described in Example 2, except that Cryptosporidium was obtained in highly concentrated form from infected calves. Rabbits were immunized following conventional methods. Antibodies were prepared using standard techniques. These antibodies were labelled following the protocol described in Example 3.

The procedure followed is as described above for OW3, except that 17.6 $\mu$g (11.7 $\mu$l of a 1.5 $\mu$g/$\mu$l solution prepared from the 75 $\mu$g TAG product) of the ORIGEN TAG-NHS Ester is added to the protein solution.

Example 4

BIOTINYLATION OF OW3 ANTIGEN 1.5 mg of OW3 antibody is dissolved in 1.5 ml of 150 mM potassium phosphate buffer, pH 7.8, containing 150 mM sodium chloride, and Aliquoted into 0.5 ml fractions.

1 mg of ORIGEN Biotin-LC-Sulfo-NHS Ester in 0.5 ml of sterile, distilled water is dissolved immediately prior to use resulting in a 2 mg/ml solution. To achieve a molar ratio of 10:1, 20:1 or 40:1 ORIGEN Biotin-LC-NHS ester to 0.5 mg of antibody in 0.5 ml of buffer, 9.3, 18.5, or 37 $\mu$l, of the biotinylation reagent, respectively, are added to the antibody aliquots. The solution is incubated for 60 minutes at room temperature, and quenched by the addition of 20 $\mu$l of 2 M glycine.

Unreacted ORIGEN Biotin-LC-Sulfo-NHS Ester is removed by dialyzing the antibody solution against the desired final buffer of PBS containing 0.02% NaN$_3$. Gel filtration on an appropriate size desalting column (such as a PD-10 disposable column from Pharmacia) or spin column, or use a microcentrator such as a Centricon-30 (Amicon) can also be employed to remove unreacted ORIGEN Biotin-LC-Sulfo-NHS Ester.

The biotinylated antibody is stored at 4° C. until ready for use.

BIOTINYLATION OF 3E3 ANTIBODY

This procedure is as described above for the OW3 antibody.

Example 5

ASSAY FOR OOCYST ANTIGENS

A 30 microliter sample of treated sludge (Example 2) is pippetted into a 12×70 mm test tube. 25 microliters of a 2 mg/ml solution of the biotinylated OW3 antibody (Example 4) in ORIGEN Assay Diluent (available from IGEN) is added to the tube, followed by the addition of 25 microliters of 2 mg/ml solution of the TAG-labelled OW3 antibody in ORIGEN Assay Diluent (Example 3). The mixture is incubated at 37° C. for 2 hours, mixing periodically. Following incubation, 25 microliters of a 1 mg/ml suspension of Dynal 2.8 micron streptavidin coated beads (equivalent to 25 micrograms) in ORIGEN Assay Diluent is added. The mixture is again incubated for 30 minutes at room temperature. The immunoassay incubation mixture is then diluted to 300 microliters with ORIGEN Assay Buffer.

The tube is placed in the carousel of the ORIGEN Analyzer and the test cycle started. Using a peristaltic pump, the instrument draws an aliquot of the sample from the carousel tube and transports it to the electrochemical flow cell. The paramagnetic beads are collected at the electrode by a magnet associated with the flow cell. Thereafter a voltage is applied to the electrode. Light produced by the TAG is detected or quantitated by a photomultiplier.

The immunoassay is calibrated by assaying for known quantities of Cryptosporidium oocysts counted by generally accepted procedures using a flow cytometer. The calibrator solution is prepared from freshly isolated oocyst from the stool of infected patients.

ASSAY FOR SPOROZOITE ANTIGEN

The assay procedure for the sporozoite antigen is as described above for the occyst antigen assay except using 3E3 antibody.

The immunoassay is calibrated by assaying for known quantities of Cryptosporidium occysts containing live sporozoites. The calibrator solution is prepared from freshly isolated oocysts from the stool of infected patients and counted by generally accepted procedures using a flow cytometer.

Example 6

CONTEMPORANEOUS ASSAY FOR OOCYST AND SPOROZOITE ANTIGEN

The ECL immunoassays of examples 7 and 8 can be performed contemporaneously (either simultaneously or in rapid succession). The concentrate derived in example 1 is solubilized as described in example 2. The solubilized product is divided into two equal portions. The portions are then assayed using the methods described in Examples 3 through 5.

What is claimed is:

1. A method for the detection or quantitation of Cryptosporidia in a water sample comprising:
    (a) filtering said water sample to obtain a retentate comprising oocysts and/or sporozoites of Cryptosporidia present in the water sample;
    (b) extracting said retentate in an extraction medium;
    (c) solubilizing, in said extraction medium, an antigen of said oocysts and/or sporozoites;
    (d) forming an assay mixture comprising,
        (i) said solubilized antigen and
        (ii) an antibody specific to said antigen;
    (e) incubating said assay mixture under conditions sufficient to permit binding of said antibody and said antigen thereby forming an antibody-antigen complex; and
    (f) determining the presence of said antibody-antigen complex, thereby detecting or quantitating Cryptosporidia in said water sample.

2. A method for the detection or quantitation of Cryptosporidia in a sample comprising:
   (a) extracting the sample in an extraction medium;
   (b) solubilizing, in said extraction medium, an antigen of Cryptosporidia oocysts and/or sporozoites;
   (c) forming an assay mixture comprising,
      (i) said solubilized antigen and
      (ii) an antibody specific to said antigen;
   (d) incubating said assay mixture under conditions sufficient to permit binding of said antibody and said antigen thereby forming an antibody-antigen complex; and
   (e) determining the presence of said antibody-antigen complex, thereby detecting or quantitating Cryptosporidia in the sample.

3. The method of claim 2, wherein said antibody is linked to a label.

4. The method of claim 2, wherein said label is biotin.

5. The method of claim 2, wherein said label is an electrochemiluminescent moiety and said antibody-antigen complex is determined by an electrochemiluminescence measurement.

6. The method of claim 2, wherein said extraction medium comprises a bile salt or an ionic detergent.

7. The method of claim 2, wherein said extraction medium is acidic.

8. The method of claim 2, wherein said solubilization is conducted at elevated temperature.

9. The method of claim 2, wherein said extraction medium comprises a bile salt or an ionic detergent and said assay mixture comprises a protein in an amount sufficient to sequester said detergent.

10. The method of claim 2, wherein said sample is a retentate formed by filtering a volume of water.

11. The method of claim 2, wherein said antigen is an oocyst outer cell wall antigen.

12. The method of claim 2, wherein said antibody is linked to a label, said assay mixture further comprises a second antibody specific for said antigen and a solid support linked or capable of capturing said second antibody, and said antibody-antigen complex further comprises said second antibody and said solid support.

13. A method for the detection or quantitation of Cryptosporidia in a water sample comprising:
   (a) filtering said water sample to obtain a retentate comprising Cryptosporidia present in the water sample
   (b) extracting the retentate in an extraction medium;
   (c) solubilizing, in said extraction medium, antigens of oocysts of said Cryptosporidia, including at least one first antigen from the outer wall of said oocysts and at least one second antigen of a sporozoite contained within said oocyst;
   (d) forming a first assay mixture comprising,
      (i) a first portion of said solubilized antigens, and
      (ii) a first antibody specific to said first antigen;
   (e) forming a second assay mixture comprising,
      (i) a second portion of said solubilized antigens, and
      (ii) a second antibody specific to said second antigen;
   (f) incubating said first assay mixture under conditions sufficient to permit binding of said first antibody and said first antigen forming a first antibody-antigen complex;
   (g) incubating said second assay mixture under conditions sufficient to permit binding of said second antibody and said second antigen thereby forming a second antibody-antigen complex;
   (h) determining the presence of said first antibody-antigen complex;.and
   (i) determining the presence of said second antibody-antigen complex, thereby detecting or quantitating both the oocysts and sporozoites in the sample.

14. A method for the detection or quantitation of Cryptosporidia in a sample comprising:
   (a) extracting the sample in an extraction medium;
   (b) solubilizing, in said extraction medium, antigens of oocysts of said Cryptosporidia, including at least one first antigen from the outer wall of said oocysts and at least one second antigen of a sporozoite contained within said oocyst;
   (c) forming a first assay mixture comprising,
      (i) a first portion of said solubilized antigens, and
      (ii) a first antibody specific to said first antigen;
   (d) forming a second assay mixture comprising,
      (i) a second portion of said solubilized antigens, and
      (ii) a second antibody specific to said second antigen;
   (e) incubating said first assay mixture under conditions sufficient to permit binding of said first antibody and said first antigen forming a first antibody-antigen complex;
   (f) incubating said second assay mixture under conditions sufficient to permit binding of said second antibody and said second antigen thereby forming a second antibody-antigen complex;
   (g) determining the presence of said first antibody-antigen complex; and
   (h) determining the presence of said second antibody-antigen complex, thereby detecting or quantitating both the oocysts and sporozoites in the sample.

15. A method for the detection or quantitation of Cryptosporidia in a water sample comprising:
   (a) filtering said water sample to obtain a retentate comprising oocysts and/or sporozoites of Cryptosporidia present in the water sample;
   (b) extracting said retentate in an extraction medium
   (c) solubilizing, in said extraction medium, an antigen of said oocysts and/or sporozoites;
   (d) forming an assay mixture comprising,
      (i) said solubilized antigen,
      (ii) a capture antibody specific to said antigen,
      (iii) a label probe comprising a label antibody specific to said antigen and an electrochemiluminescent moiety, and
      (iv) a magnetic particle linked to or capable of capturing said capture antibody;
   (e) incubating said assay mixture under conditions sufficient to form a complex comprising said magnetic particle, said capture antibody, said antigen and said label probe; and
   (f) conducting an electrochemiluminescence assay for said complex, thereby detecting or quantitating Cryptosporidia in said water sample.—

16. A method for the detection or quantitation of Cryptosporidia in a sample comprising:
   (a) extracting said sample in an extraction medium;
   (b) solubilizing, in said extraction medium, an antigen of said oocysts and/or sporozoites;
   (c) forming an assay mixture comprising,
      (i) said solubilized antigen,
      (ii) a capture antibody specific to said antigen,
      (iii) a label probe comprising a label antibody specific to said antigen and an electrochemiluminescent moiety, and (iv) a magnetic particle linked to or capable of capturing said capture antibody;

(d) incubating said assay mixture under conditions sufficient to form a complex comprising said magnetic particle, said capture antibody, said antigen and said label probe; and (e) conducting an electrochemiluminescence assay for said complex, thereby detecting or quantitating Cryptosporidia in said sample.

17. A method for the detection or quantitation of Cryptosporidia in a water sample comprising:

(a) filtering said water sample to obtain a retentate comprising Cryptosporidia present in the water sample (b) extracting the retentate in an extraction medium;

(c) solubilizing, in said extraction medium, antigens of oocysts of said Cryptosporidia, including at least one first antigen from the outer wall of said oocysts and at least one second antigen of a sporozoite contained within said oocyst;

(d) forming a first assay mixture comprising,
  (i) a first portion of said solubilized antigens,
  (ii) a first capture antibody specific to said first antigen,
  (iii) a first label probe comprising a first label antibody specific to said first antigen and a first electrochemiluminescent moiety, and
  (iv) a first magnetic particle linked to or capable of capturing said first capture antibody;

(e) forming a second assay mixture comprising,
  (i) a second portion of said solubilized antigens,
  (ii) a second capture antibody specific to said second antigen,
  (iii) a second label probe comprising a second label antibody specific to said second antigen and a second electrochemiluminescent moiety, and
  (iv) a second magnetic particle linked to or capable of capturing said second capture antibody;

(f) incubating said first assay mixture under conditions sufficient to form a first complex comprising said first magnetic particle, said first capture antibody, said first antigen and said first label probe;

(g) incubating said second assay mixture under conditions sufficient to form a second complex comprising said second magnetic particle, said second capture antibody, said second antigen and said second label probe;

(h) determining the presence of said first complex; and (i) determining the presence of said second complex, thereby detecting or quantitating both the oocysts and sporozoites in the water sample.

18. A method for the detection or quantitation of Cryptosporidia in a sample comprising:

(a) extracting the sample in an extraction medium;

(b) solubilizing, in said extraction medium, antigens of oocysts of said Cryptosporidia, including at least one first antigen from the outer wall of said oocysts and at least one second antigen of a sporozoite contained within said oocyst;

(c) forming a first assay mixture comprising,
  (i) a first portion of said solubilized antigens,
  (ii) a first capture antibody specific to said first antigen,
  (iii) a first label probe comprising a first label antibody specific to said first antigen and a first electrochemiluminescent moiety, and
  (iv) a first magnetic particle linked to or capable of capturing said first capture antibody;

(d) forming a second assay mixture comprising,
  (i) a second portion of said solubilized antigens,
  (ii) a second capture antibody specific to said second antigen,
  (iii) a second label probe comprising a second label antibody specific to said second antigen and a second electrochemiluminescent moiety, and
  (iv) a second magnetic particle linked to or capable of capturing said second capture antibody;

(e) incubating said first assay mixture under conditions sufficient to form a first complex comprising said first magnetic particle, said first capture antibody, said first antigen and said first label probe;

(f) incubating said second assay mixture under conditions sufficient to form a second complex comprising said second magnetic particle, said second capture antibody, said second antigen and said second label probe;

(g) determining the presence of said first complex; and (h) determining the presence of said second complex, thereby detecting or quantitating both the oocysts and sporozoites in the sample.

19. A composition of matter comprising:

(a) a retentate formed by filtering a water sample;

(b) an extraction medium comprising at least one surfactant in an amount effective to solubilize at least one antigen of Cryptosporidia oocyst; and (c) a complex comprising said antigen and an antibody specific for said antigen.

20. The composition of claim 19, wherein said surfactant is a bile salt or an ionic detergent.

21. The composition of claim 19, wherein said antigen is an oocyst outer cell wall antigen.

22. The composition of claim 19, wherein the pH of said composition is less than 4.

23. A kit for quantifying Cryptosporidia in a sample comprising in one or more containers:

(a) an extraction medium comprising at least one bile salt or ionic detergent in an amount effective to solubilize at least one cell wall antigen from Cryptosporidia oocyst, and (b) an antibody specific to said antigen.

24. The kit of claim 23, wherein said antibody is labeled with biotin.

25. The kit of claim 23, wherein said antibody is labeled with an electrochemiluminescent moiety.

26. The kit of claim 23, wherein said antibody is OW3.

27. The kit of claim 23, wherein said cell wall antigen is the antigen recognized by a OW3 antibody.

28. The kit of claim 23, further comprising a buffered protein-containing assay diluent.

29. A kit for quantifying Cryptosporidia in a sample comprising in one or more containers:

(a) an extraction medium comprising at least one bile salt or ionic detergent in an amount effective to solubilize at least one cell wall antigen from oocysts of Cryptosporidia;

(b) a capture antibody specific for said antigen;

(c) a label antibody specific for said antigen; and (d) a solid support linked to or capable of capturing said capture antibody.

30. The kit of claim 29, wherein said capture antibody is labeled with biotin, said label antibody is labeled with an electrochemiluminescent label, and said solid support is a streptavidin-coated magnetic bead.

31. The kit of claim 29, further comprising a buffered protein-containing assay diluent.

* * * * *

UNITED STATES PATENT AND TRADEMARK OFFICE
CERTIFICATE OF CORRECTION

PATENT NO. : 6,146,838
DATED : November 14, 2000
INVENTOR(S) : Williams et al.

Page 1 of 1

It is certified that error appears in the above-identified patent and that said Letters Patent is hereby corrected as shown below:

<u>Column 13,</u>
Line 47, add -- ; -- after "sample"

<u>Column 14,</u>
Line 2, change "complex;.and" to -- complex; and --
Line 38, add -- ; -- after "medium"

<u>Column 15,</u>
Line 12, add -- ; -- after "sample"

<u>Column 16,</u>
Line 38, change "oocyst, and" to -- oocyst; and --

Signed and Sealed this

Eighteenth Day of December, 2001

*Attest:*

JAMES E. ROGAN
*Attesting Officer*   *Director of the United States Patent and Trademark Office*